US010993614B2

(12) United States Patent
Charles

(10) Patent No.: US 10,993,614 B2
(45) Date of Patent: May 4, 2021

(54) OCT-ENABLED INJECTION FOR VITREORETINAL SURGERY

(71) Applicant: NOVARTIS AG, Basel (CH)

(72) Inventor: Steven T. Charles, Germantown, TN (US)

(73) Assignee: Alcon Inc., Fribourg (CH)

( * ) Notice: Subject to any disclaimer, the term of this patent is extended or adjusted under 35 U.S.C. 154(b) by 219 days.

(21) Appl. No.: 16/150,803

(22) Filed: Oct. 3, 2018

(65) Prior Publication Data
US 2019/0110682 A1  Apr. 18, 2019

Related U.S. Application Data

(60) Provisional application No. 62/572,599, filed on Oct. 16, 2017.

(51) Int. Cl.
| *A61B 3/13* | (2006.01) |
| *A61F 9/007* | (2006.01) |
| *A61B 3/10* | (2006.01) |
| *A61B 3/12* | (2006.01) |
| *A61B 90/00* | (2016.01) |
| *A61B 90/20* | (2016.01) |
| *A61B 3/00* | (2006.01) |
| *A61B 5/00* | (2006.01) |
| *A61B 34/20* | (2016.01) |
| *A61B 17/00* | (2006.01) |

(52) U.S. Cl.
CPC ............. *A61B 3/132* (2013.01); *A61B 3/102* (2013.01); *A61B 3/12* (2013.01); *A61B 90/20* (2016.02); *A61B 90/37* (2016.02); *A61F 9/00736* (2013.01); *A61B 3/0041* (2013.01); *A61B 5/0066* (2013.01); *A61B 2017/00203* (2013.01); *A61B 2017/00207* (2013.01); *A61B 2017/00216* (2013.01); *A61B 2034/2065* (2016.02); *A61B 2090/372* (2016.02); *A61B 2090/3735* (2016.02); *G06T 2207/10101* (2013.01); *G06T 2207/30041* (2013.01)

(58) Field of Classification Search
CPC ......... A61B 3/132; A61B 90/20; A61B 3/102; A61B 3/12; A61B 90/37; A61B 2034/2065; A61B 2017/00207; A61B 2017/00203; A61B 2017/00216; A61B 2090/372; A61B 3/0041; A61B 5/0066; A61B 2090/3735; A61F 9/00736; G06T 2207/30041; G06T 2207/10101
USPC ................................ 351/41, 159.01, 159.02
See application file for complete search history.

(56) References Cited

U.S. PATENT DOCUMENTS

| 6,024,719 | A  | * | 2/2000 | Morris ................. A61M 25/00 |
| | | | | 604/28 |
| 9,560,959 | B1 | | 2/2017 | Hopkins |
| 9,579,017 | B2 | | 2/2017 | Heeren |
| 9,675,244 | B1 | | 6/2017 | Ren |

(Continued)

FOREIGN PATENT DOCUMENTS

| KR | 101769914 B1 | 8/2017 |
| WO | WO2004023992 A1 | 3/2004 |

*Primary Examiner* — Tuyen Tra

(57) ABSTRACT

OCT-enabled injection for vitreoretinal surgery may involve using an OCT image to detect when a surgical injector penetrates a desired tissue layer of the eye for receiving an injection. The injection may be triggered or automatically actuated based on the detection of the surgical injector from the OCT image.

10 Claims, 3 Drawing Sheets

(56) References Cited

U.S. PATENT DOCUMENTS

| | | |
|---|---|---|
| 9,717,405 B2 | 8/2017 | Ren |
| 9,826,900 B2 | 11/2017 | Heeren |
| 9,844,314 B2 | 12/2017 | Charles |
| 10,064,549 B2 | 9/2018 | Charles |
| 10,132,748 B2 | 11/2018 | Helfmann |
| 10,188,808 B2 | 1/2019 | Kang |
| 10,285,584 B2 | 5/2019 | Charles |
| 10,398,307 B2 | 9/2019 | Charles |
| 10,517,760 B2 | 12/2019 | Berlin |
| 2012/0197102 A1* | 8/2012 | Hanebuchi ............... A61F 2/16 600/398 |
| 2014/0221822 A1 | 8/2014 | Ehlers et al. |
| 2015/0030542 A1 | 1/2015 | Singhal |
| 2015/0342460 A1 | 12/2015 | Izatt |
| 2017/0045721 A1 | 2/2017 | Charles |
| 2017/0135573 A1 | 5/2017 | Charles |
| 2017/0280989 A1 | 10/2017 | Heeren |
| 2018/0028356 A1* | 2/2018 | Murata ................. A61F 9/0017 |
| 2018/0228552 A1* | 8/2018 | Milner .................. A61B 3/102 |
| 2018/0299658 A1 | 10/2018 | Carrasco-zevallos |
| 2018/0323553 A1* | 11/2018 | Wagner .................... G05G 1/02 |
| 2018/0360310 A1* | 12/2018 | Berlin ..................... A61F 9/008 |
| 2019/0105197 A1 | 4/2019 | Labelle |
| 2019/0125182 A1 | 5/2019 | Charles |
| 2019/0175402 A1 | 6/2019 | Eil et al. |
| 2019/0328458 A1* | 10/2019 | Shmayahu ............. A61B 5/064 |

\* cited by examiner

400 — METHOD FOR OCT-ENABLED INJECTION DURING VITREORETINAL SURGERY

402 — DURING VIEWING OF AN INTERIOR PORTION OF AN EYE OF A PATIENT USING AN OPHTHALMIC VISUALIZATION SYSTEM, RECEIVE A FIRST INDICATION FROM A USER OF THE SURGICAL MICROSCOPE OF A LOCATION IN THE EYE FOR RECEIVING AN INJECTION OF A SUBSTANCE

404 — BASED ON THE FIRST INDICATION, INITIATE OCT SCANNING OF THE LOCATION, THE OCT SCANNING ENABLED TO CONTINUOUSLY GENERATE AN OCT IMAGE OF TISSUE LAYERS AT THE LOCATION

406 — CAUSE THE OCT IMAGE TO BE DISPLAYED TO THE USER

408 — RECEIVE A SECOND INDICATION FROM THE USER TO PERFORM THE INJECTION AT THE LOCATION, WHERE THE SECOND INDICATION SPECIFIES A TISSUE LAYER FROM THE OCT IMAGE FOR RECEIVING THE INJECTION AND A VOLUME OF THE SUBSTANCE TO BE INJECTED

410 — BASED ON THE SECOND INDICATION, DETECT A SURGICAL INJECTOR AT THE LOCATION FROM THE OCT IMAGE, INCLUDING DETECTING WHETHER THE SURGICAL INJECTOR PENETRATES THE TISSUE LAYER

412 — DOES THE SURGICAL INJECTOR PENETRATE THE TISSUE LAYER? NO (loop back) / YES 414 — CAUSE THE INJECTION TO BE PERFORMED BY THE SURGICAL INJECTOR, WHERE THE SURGICAL INJECTOR INJECTS THE SUBSTANCE INTO THE TISSUE LAYER 416 — CAUSING A FEEDBACK INDICATION TO BE OUTPUT TO THE USER, THE FEEDBACK INDICATION INDICATING CONFIRMATION OF THE INJECTION OF THE VOLUME

FIG. 4

OCT-ENABLED INJECTION FOR VITREORETINAL SURGERY

PRIORITY CLAIM

This application claims the benefit of priority of U.S. Provisional Patent Application Ser. No. 62/572,599 titled "OCT-ENABLED INJECTION FOR VITREORETINAL SURGERY", filed on Oct. 16, 2017, whose inventor is Steven T. Charles, which is hereby incorporated by reference in its entirety as though fully and completely set forth herein.

FIELD OF THE DISCLOSURE

The present disclosure relates to ophthalmic surgery, and more specifically, to OCT-enabled injection for vitreoretinal surgery.

BACKGROUND

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus. During a procedure, the field of view of the fundus may be presented to and viewed by the ophthalmologist using an ophthalmic visualization system which may include a microscope-based or microscope-less optical system such as NGENUITY® (Alcon Laboratories, Inc.).

In addition to optics for viewing the fundus, surgical microscopes may be equipped with optical coherence tomography (OCT) scanners to provide additional information about portions of eye tissue involved with the vitreoretinal surgery. The OCT scanner may enable imaging below a visible surface of the eye tissue during vitreoretinal surgery.

For certain therapies, a surgical injector may be used to inject a substance into the eye, such as into an intraretinal or subretinal tissue layer. Because of the very small dimensions of certain tissue layers in the eye, manual actuation of the surgical injector may not be feasible or desirable, because any movement by the surgeon to perform the manual actuation may inherently cause the surgical injector to be displaced in an undesirable manner.

SUMMARY

In one aspect, a disclosed method is for injecting substances during ophthalmic surgery. During viewing of an interior portion of an eye of a patient using an ophthalmic visualization system, the method may include receiving a first indication from a user of the ophthalmic visualization system of a location in the eye for receiving an injection of a substance. Based on the first indication, the method may include initiating OCT scanning of the location, the OCT scanning enabled to continuously generate an OCT image of tissue layers at the location. In the method, the OCT scanning may be performed by an OCT scanner that is optically coupled to the ophthalmic visualization system. The method may further include causing the OCT image to be displayed to the user, and receiving a second indication from the user to perform the injection at the location. In the method, the second indication may specify a tissue layer from the OCT image for receiving the injection and a volume of the substance to be injected. Based on the second indication, the method may include detecting a surgical injector at the location from the OCT image, including detecting whether the surgical injector penetrates the tissue layer. When the surgical injector penetrates the tissue layer, the method may include causing the injection to be performed by the surgical injector. In the method, the surgical injector may inject the volume of the substance into the tissue layer.

In any of the disclosed implementations of the method, receiving the second indication may further include receiving final approval for automatically causing the injection to be performed based only on detecting that the surgical injector has penetrated the tissue layer.

In any of the disclosed implementations of the method, receiving the second indication may further include receiving a confirmation from the user that the surgical injector is being armed to automatically perform the injection.

In any of the disclosed implementations of the method, the location may be in a posterior portion of the interior portion of the eye.

In any of the disclosed implementations of the method, the tissue layer may be one of: an intraretinal layer; and a subretinal layer.

In any of the disclosed implementations of the method, the surgical injector may be on of a metal syringe needle, a polymer needle, a metal cannula, and a polymer cannula, while the OCT image may be one of a B-scan image and an en face image.

In any of the disclosed implementations of the method, causing the OCT image to be displayed to the user may further include causing the OCT image to be displayed to the user in a surgical field of the ophthalmic visualization system.

In any of the disclosed implementations of the method, the substance may include at least one of: cells, photoreceptor aggregates, viral vectors, nucleic acids, proteins, peptides, peptidomimetics, small molecules, large molecules, nanostructures and nanoparticles.

In any of the disclosed implementations, the method may further include, after causing the OCT image to be displayed to the user, enabling the user to specify the tissue layer using the OCT image.

In any of the disclosed implementations, the method may further include, after the surgical injector injects the volume of the substance into the tissue layer, causing a feedback indication to be output to the user, the feedback indication indicating confirmation of the injection of the volume and comprising at least one of: an audio alert; and a visual alert in a surgical field of the ophthalmic visualization system.

Additional disclosed implementations include an OCT scanning controller, an ophthalmic visualization system, a surgical microscope, and an image processing system.

BRIEF DESCRIPTION OF THE DRAWINGS

For a more complete understanding of the present disclosure, reference is now made to the following description, taken in conjunction with the accompanying drawings, in which:

FIG. 4 is a flow chart of selected elements of a method for OCT-enabled injection during vitreoretinal surgery.

DETAILED DESCRIPTION

Figure 1:
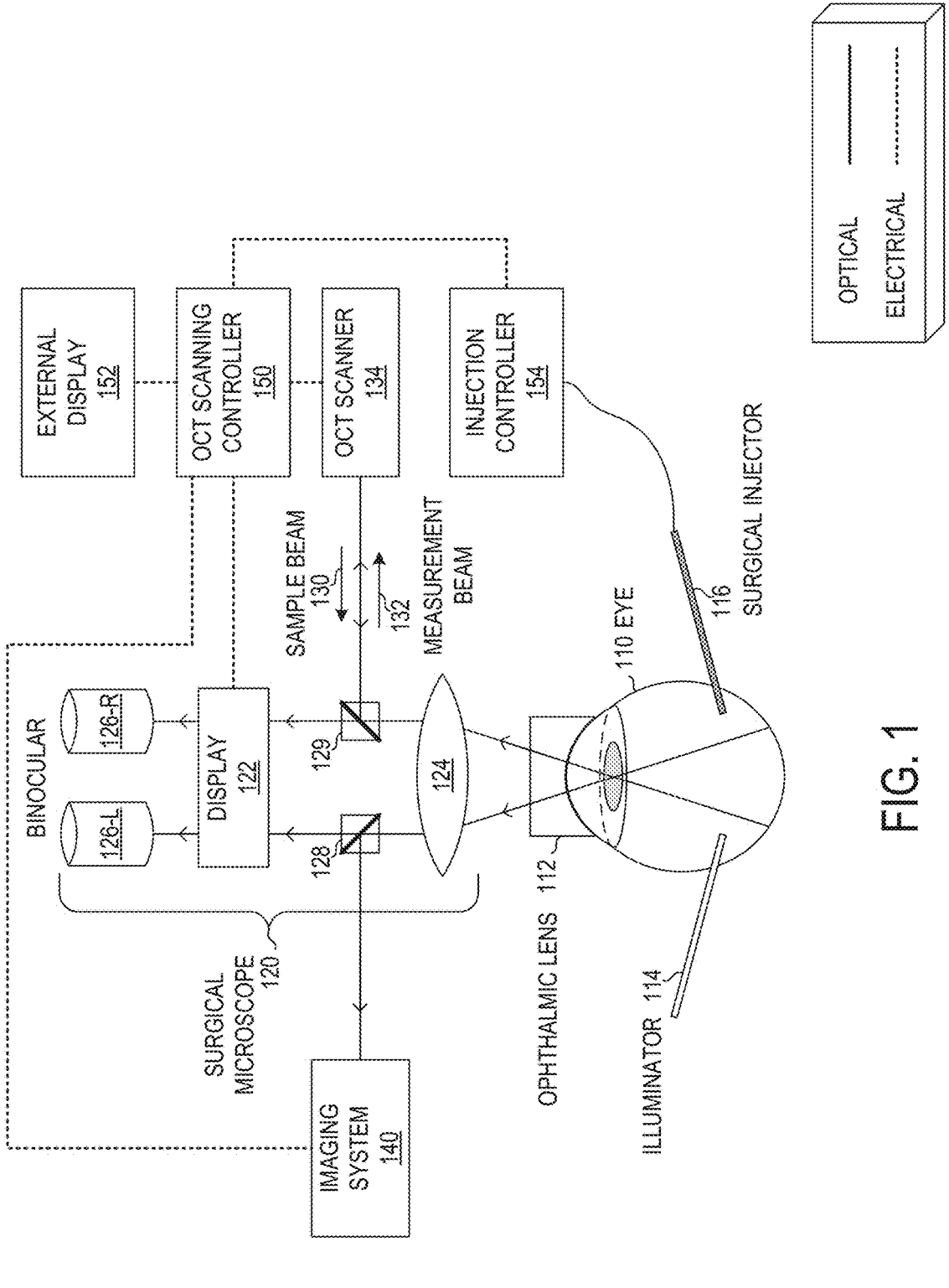
FIG. 1 is a block diagram of selected elements of an implementation of a surgical microscopy scanning instrument.

In the following description, details are set forth by way of example to facilitate discussion of the disclosed subject matter. It should be apparent to a person of ordinary skill in the field, however, that the disclosed implementations are exemplary and not exhaustive of all possible implementations.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with an ophthalmic lens for viewing through the cornea, such as a contact or non-contact lens. In order to perform any of a variety of surgical procedures, the surgeon may desire to optically scan certain portions of the fundus to generate profile depth scans of the corresponding eye tissue, such as by using an OCT scanner. The profile depth scans may reveal information about eye tissue that is not readily visible from optical images generated by the surgical microscope. The profile depth scans may be point scans (A-scan), line scans (B-scan), or area scans (C-scan). An image from a B-scan will image the depth of eye tissue along a line, while a C-scan results in 3-dimensional (3D) data that can be sectioned to provide various views, including an en face view from the optical view perspective, but which can be generated at various depths and for selected tissue layers.

Furthermore, various new treatments, such as gene therapy, cell-based therapies (including stem cell therapies), and cytokine injections for retinal and retinal pigment epithelium (RPE) disorders, may involve intraretinal or subretinal injection to produce high levels of transfection (gene therapy), pharmacologic effect (selected cytokines), synaptic connections (stem cells), or polarized RPE monolayers (stem cells). In addition, it has been observed that subretinal gene therapy may produce a decreased inflammatory response compared to intravitreal injection.

However, the retina is very thin (200-300 microns) and the subretinal "space" is a potential space, which may be created or affected by the injection itself. Accordingly, the precise and accurate depth positioning of various surgical injectors, such as micro-cannulas, micro-needles, micropipettes, pulsed fluid injectors, electroporation devices, and other microinjection devices, is critical to the safety and efficacy of such injections during surgery. As noted, because of the very small dimensions of certain tissue layers in the eye, manual actuation of the surgical injector may not be feasible or desirable, because any movement by the surgeon to perform the manual actuation may inherently cause the surgical injector to be displaced in an undesirable manner. For example, any minute foot, hand, or other movements by the surgeon while the surgical injector is being positioned, even when the movement involves other body parts than the hand that is manipulating the surgical injector, have been observed to cause undesired displacement of the surgical injector.

The present disclosure relates to the use of OCT scanning integrated within a surgical microscope for OCT-enabled injection during vitreoretinal surgery. Specifically, the auto-segmentation ability of OCT is used to resolve tissue layers in depth within the retina as well as at the RPE-photoreceptor junction. Then, the OCT system is enabled to automatically perform the injection, when armed and confirmed by the user. Accordingly, embodiments of the disclosure may provide precise and accurate depth positioning of various surgical injectors within the eye.

As will be described in further detail, OCT-enabled injection for vitreoretinal surgery, according to certain implementations, uses an OCT image for precision injection depth sensing and actuation of a surgical injector. The OCT image may be a B-scan image or an en face image and may be displayed to the user, such as in the surgical field of the surgical microscope. Specifically, the OCT image is used to determine an injection depth in real time upon performing an OCT scan co-aligned with the surgical injector, as indicated by the user. The OCT image may be overlaid in the surgical field displayed using an imaging system and may be used to receive user input from the user specifying the precise location of the injection in the eye tissue. The user input may further specify an injection volume for the amount of substance to be injected. Additionally, a feedback indication may be provided to the user when the injection tip is at the correct depth and is within the tissue layer specified by the user. The feedback indication may be an audible indication or a visual/graphical indication, such as an overlay indication in the surgical field of view. When automatic injection is activated, such that the surgical injector is armed to automatically perform the injection when the tip of the surgical injector is detected at the specified tissue layer, the feedback indication may include a confirmation of the volume actually injected, such as an audio feedback or a visual feedback displayed in the surgical field of the surgical microscope.

Referring now to the drawings, FIG. 1 is a block diagram showing a surgical microscopy scanning instrument 100. Instrument 100 is not drawn to scale but is a schematic representation. As will be described in further detail, instrument 100 may be used during vitreoretinal surgery to view and analyze a human eye 110, and for OCT-enabled injection during vitreoretinal surgery, as disclosed herein. As shown, instrument 100 includes surgical microscope 120, OCT scanning controller 150, external display 152, OCT scanner 134, and injection controller 154. Also shown in FIG. 1 are imaging system 140, ophthalmic lens 112, as well as surgical injector 116 and illuminator 114.

As shown, an example surgical microscope 120 is depicted in schematic form to illustrate optical functionality. It will be understood that embodiments of surgical microscope 120 may include various other electronic and mechanical components, in different implementations. It is noted that, in various embodiments, instrument 100 may include any suitable ophthalmic visualization system in addition to or in lieu of surgical microscope 120, including a microscope-free visualization platform such as NGENU-ITY®. Accordingly, while the particular optical design discussed with reference to FIG. 1 is specific to an ophthalmic visualization system that comprises microscope 120, one skilled in the art will appreciate that alternative optical arrangements to support other ophthalmic visualization systems are within the scope of the disclosure.

In the example shown in FIG. 1, objective 124 may represent a selectable objective to provide a desired magnification or field of view of the fundus. Objective 124 may receive light from the fundus of eye 110 via ophthalmic lens 112 that rests on a cornea of eye 110. It is noted that various types of ophthalmic lenses 112 may be used with surgical microscope 120, including contact lenses and non-contact lenses. To perform vitreoretinal surgery, various tools and instruments may be used, including tools that penetrate the sclera, such as surgical injector 116 that can inject a desired volume of a substance. In particular embodiments, surgical injector 116 may penetrate the eye with a syringe needle that may be used for microinjection, such as a 20 gage needle, a 22 gage needle, a 24 gage needle, or a 28 gage needle, among other sizes (see also FIG. 3). Illuminator 114 may be a special tool that provides a light source from within the fundus of eye 110.

In FIG. 1, surgical microscope 120 is shown with a binocular arrangement with two distinct but substantially equal light paths that enable viewing with binoculars 126 that comprise a left ocular 126-L and a right ocular 126-R. From objective 124, a left light beam may be split at beam splitter 128, from where imaging system 140 and left ocular 126-L receive the optical image. Also from objective 124, a right light beam may be split at partial mirror 129, which also receives sample beam 130 from OCT scanner 134, and outputs measurement beam 132 to OCT scanner 134. Partial mirror 129 also directs a portion of the right light beam to right ocular 126-R. Display 122 may represent an optoelectronic component, such as an image processing system that receives the data from OCT scanning controller 150 and generates image output for left ocular 126-L and right ocular 126-R, respectively. In some implementations, display 122 includes miniature display devices that output images to binoculars 126 for viewing by the user. It is noted that the optical arrangement depicted in FIG. 1 is exemplary and may be implemented differently in other implementations. For example, the left and right beams may be reversed or combined in different implementations.

As described above, the optical system in surgical microscope 120 using binoculars 126 may provide a certain degree of depth visualization or 3-dimensional (3-D) display capability. Although integration of OCT with surgical microscope 120 is shown in FIG. 1 using an analog optical system, it will be understood that another ophthalmic visualization system may be used in addition to or in lieu of surgical microscope 120 in various implementations. For example, instead of integrating display 122 within binoculars 126, the ophthalmic visualization system used with instrument 100 may be implemented digitally without binoculars 126 and by using an image sensor for each of the left beam and the right beam, such as a video camera. The left and right images from the respective image sensors may be used to generate a 3-D capable display that is viewed on a corresponding monitor, such as external display 152, rather than using binoculars 126, which may be omitted in a digital implementation of the ophthalmic visualization system. In certain implementations, surgical microscope 120 as depicted in FIG. 1 may be accordingly implemented using NGENU-ITY® 3D Visualization System (Alcon Laboratories, Inc.), which provides a platform for digitally assisted vitreoretinal surgery (DAVS).

In FIG. 1, OCT scanning controller 150 may have an electrical interface with display 122, for example, for outputting display data. In this manner, OCT scanning controller 150 may output a display image to display 122 that is viewed at binoculars 126. Because the electrical interface between imaging system 140 and OCT scanning controller 150 may support digital image data, OCT scanning controller 150 may perform image processing in real-time with relatively high frame refresh rates, such that a user of surgical microscope 120 may experience substantially instantaneous feedback to user input for controlling the selected portion of eye 110 for scanning, as well as other operations, as disclosed herein. External display 152 may output similar images as display 122, but may represent a stand-alone monitor for viewing by various personnel during vitreoretinal surgery. Display 122 or external display 152 may be implemented as a liquid crystal display screen, a computer monitor, a television, a tablet, a touchscreen, a 3-D visualization system, a projector, viewing glasses or goggles, or the like. Display 122 or external display 152 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 120 in FIG. 1, imaging system 140 may receive a portion of the left light beam that enables imaging system 140 to independently process, display, store, and otherwise manipulate light beams and image data. In certain embodiments, imaging system 140 may receive a portion of the right light beam, or both the left and right light beam, to enable imaging system 140 to independently process, display, store, and otherwise manipulate light beams and image data, and support 3-D visualization. Accordingly, imaging system 140 may represent any of a variety of different kinds of imaging systems, as desired.

As shown, OCT scanner 134 may represent an implementation of various kinds of OCT scanners. It is noted that other types of optical scanners may be used with the arrangement depicted in FIG. 1. OCT scanner 134 may control output of sample beam 130 and may receive measurement beam 132 that is reflected back in response to photons of sample beam 130 interacting with tissue in eye 110. OCT scanner 134 may also be enabled to move sample beam 130 to the selected location indicated by the user. OCT scanning controller 150 may interface with OCT scanner 134, for example, to send commands to OCT scanner 134 indicating the selected location to generate scan data, and to receive the scan data from OCT scanner 134. It is noted that OCT scanner 134 may represent various types of OCT instruments and configurations, as desired, such as but not limited to time domain OCT (TD-OCT) and frequency domain OCT (FD-OCT), such as spectral-domain OCT (SD-OCT) and sweptsource OCT (SS-OCT). In particular, the scan data generated by OCT scanner 134 may include two-dimensional (2D) scan data of a line scan (B-scan) and three-dimensional (3D) scan data for an area scan (C-scan). The scan data may represent a depth profile of the scanned tissue that enables imaging below a visible surface within the fundus of eye 110.

In FIG. 1, injection controller 154 may represent any of a variety of devices and injectors that are enabled for automatic or servo-driven injection of a desired volume of a substance. The substance may comprise at least one of: cells, photoreceptor aggregates, viral vectors, nucleic acids, proteins, peptides, peptidomimetics, small molecules, large molecules, nanostructures, nanoparticles, or various combinations thereof. The volume may be configurable to a desired value, and may be in the range of microliters, nanoliters, or picoliters, depending on the capabilities and dimensions of injection controller 154. Accordingly, injection controller 154 or surgical injector 116 may include a reservoir for holding the desired volume of the substance to be injected. The actuation mechanism of surgical injector 116 may be electronic, pneumatic, or hydraulic and may be triggered by a corresponding input to injection controller 154. As shown, injection controller 154 may be electronically coupled to OCT scanning controller to receive a trigger signal or indication to perform the injection, among other operations and communications.

In operation of instrument 100, the user may view the fundus of eye 110 using binoculars or external display 152 while vitreoretinal surgery is performed on eye 110. In other embodiments of instrument 100, the user may view the fundus of eye 110 using microscope-free visualization platform such as NGENUITY®. The user may provide user input in the form of a first indication to OCT scanning controller 150 to initiate an OCT scan. It is noted that a user input, indication, confirmation, or selection received by instrument 100 may be communicated using a keyboard, mouse, touch-screen, voice command, gesture, eye tracking, or other user interface coupled to scanning controller 150, injection controller 154, imaging system 140, or other components of instrument 100. The first indication may specify a location of the OCT scan in a surgical field of surgical microscope 120 where the user intends to perform an injection. OCT scanning controller 150 may, in turn, communicate with OCT scanner 134 to control scanning operations and perform a real-time OCT scan to generate first scan data at the location. The OCT scanning may be performed continuously or at a high frequency, such that the result of the OCT scan in the form of an OCT image appears to be continuously generated and updated. The OCT image may be displayed to the user using display 122, for example, to display the OCT image in the surgical field visible using binoculars 126. In some implementations, the OCT image may also or alternatively be displayed using external display 152 or a visualization platform such as NGENUITY®. In various implementations, the OCT image may be a B-scan image or an en face image. Either prior to or subsequent to display of the OCT image, the user may activate functionality for OCT-enabled injection during vitreoretinal surgery. For example, the user may select a corresponding feature provided as a menu option by OCT scanning controller to activate functionality for OCT-enabled injection during vitreoretinal surgery. The user may accordingly provide a second indication in the form of user input to OCT scanning controller to perform the injection at the location. Additionally, or with the second indication, the user may specify a tissue layer from the OCT image for receiving the injection and a volume of the substance to be injected. At this point or at a later point, the user may confirm that surgical injector 116 is being armed to automatically perform the injection. For example, the user may confirm final approval for automatically causing the injection to be performed based only on detecting that surgical injector 116 has penetrated the tissue layer. It will be understood that various kinds of user interfaces and user input options may be provided, such as the ability to cancel or suspend the injection.

Then, the user may manually insert surgical injector 116 into eye 110 for performing the injection. The user may receive additional feedback to indicate that surgical injector 116 has been identified in the OCT image, including identifying a tip of surgical injector 116. Furthermore, the user may receive feedback indicating whether the tip of surgical injector 116 has penetrated the tissue layer specified by the second indication provided by the user previously. Meanwhile, OCT scanning controller 150 may detect surgical injector 116 from the OCT image, including detecting a position of the tip of the surgical injector relative to the tissue layer. In some implementations, imaging system 140 may provide image processing capability to detect surgical injector 116. For example, imaging system 140 may execute image processing algorithms (e.g., classification, feature extraction, or pattern recognition algorithms) and/or calculate and utilize a geometrical relationship between a distal end of surgical injector 116 and the OCT image plane or c-scan (en face) layer to detect surgical injector 116 and determine the tip of the surgical injector is positioned in the tissue layer. In particular implementations, imaging system 140 may be integrated with OCT scanning controller 150.

Once surgical injector 116 has been detected to penetrate the tissue layer, such that the tip of the surgical injector is positioned in the tissue layer, OCT scanning controller 150 may trigger injection controller 154 to perform the injection using surgical injector 116. In some implementations, instead of triggering injection controller 154 for an automatic injection, OCT scanning controller 150 may output a ready indication to the user, and wait for a trigger indication in the form of user input from the user to perform the injection, before activating injection controller 154. Additionally, a display of the volume of the substance to be injected may be displayed to the user. Furthermore, after the injection is performed, a feedback indication may be provided to the user that confirms that the volume of the substance has been injected.

Modifications, additions, or omissions may be made to surgical microscopy scanning instrument 100 without departing from the scope of the disclosure. The components and elements of surgical microscopy scanning instrument 100, as described herein, may be integrated or separated according to particular applications. Surgical microscopy scanning instrument 100 may be implemented using more, fewer, or different components in some implementations.

Figure 2:
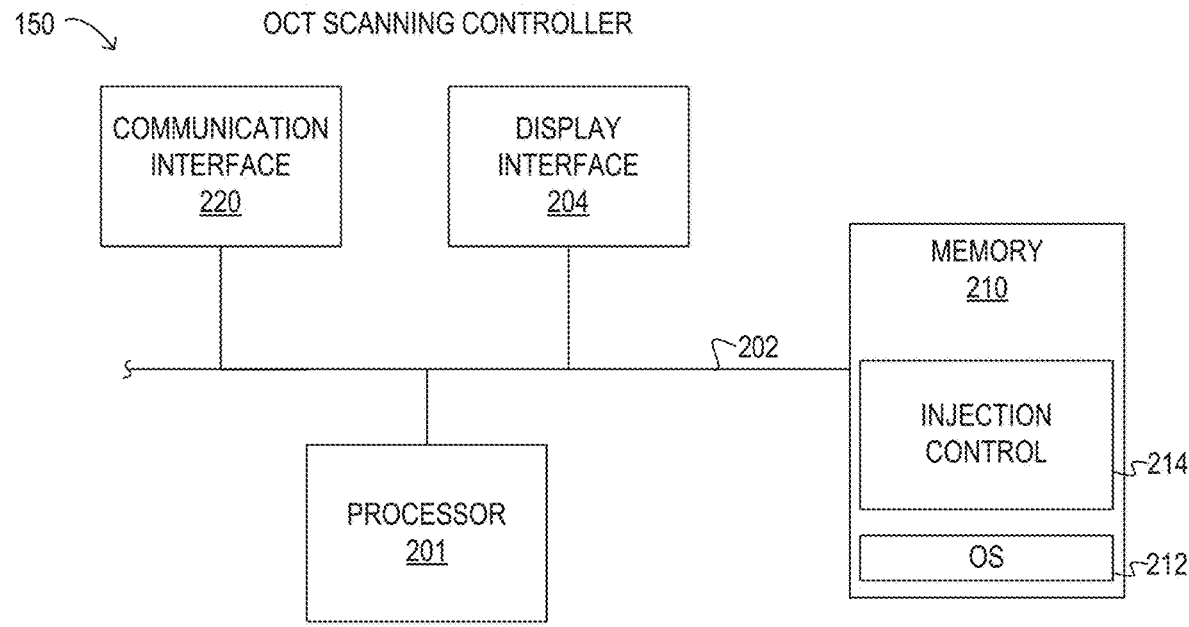
FIG. 2 is a block diagram of selected elements of an implementation of an OCT scanning controller.

Referring now to FIG. 2, a block diagram illustrating selected elements of an implementation of OCT scanning controller 150, described above with respect to FIG. 1, is presented. In the implementation depicted in FIG. 2, OCT scanning controller 150 includes processor 201 coupled via shared bus 202 to memory media collectively identified as memory 210.

OCT scanning controller 150, as depicted in FIG. 2, further includes communication interface 220 that can interface OCT scanning controller 150 to various external entities, such as OCT scanner 134 or imaging system 140, among other devices. In some implementations, communication interface 220 is operable to enable OCT scanning controller 150 to connect to a network (not shown in FIG. 2). In implementations suitable for OCT-enabled injection during vitreoretinal surgery, OCT scanning controller 150, as depicted in FIG. 2, includes display interface 204 that connects shared bus 202, or another bus, with an output port for one or more displays, such as display 122 or external display 152.

In FIG. 2, memory 210 encompasses persistent and volatile media, fixed and removable media, and magnetic and semiconductor media. Memory 210 is operable to store instructions, data, or both. Memory 210 as shown includes sets or sequences of instructions, namely, an operating system 212, and an injection control application 214. Operating system 212 may be a UNIX or UNIX-like operating system, a Windows® family operating system, or another suitable operating system. Injection control application 214 may enable OCT scanning controller 150 to perform operations for OCT-enabled injection during vitreoretinal surgery, as disclosed herein.

Although FIG. 2 depicts OCT scanning controller 150, imaging system 140 and injection controller 154 may include analogous components and features, including a bus, memory storing instructions and/or data, one or more processors, and communication interfaces.

Figure 3:
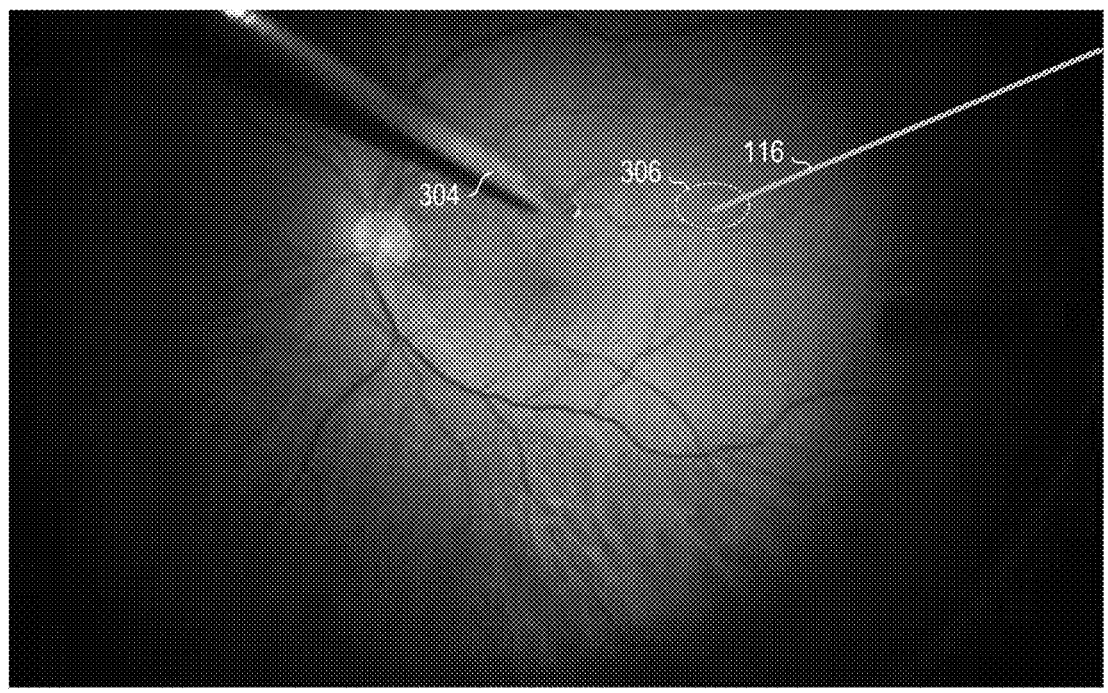
FIG. 3 is a depiction of a surgical field of view using a surgical microscopy scanning instrument.

Referring now to FIG. 3, a depiction of a surgical field 300 is shown. Surgical field 300 includes an optical image of a retina that may be viewed while performing vitreoretinal surgery using instrument 100 in FIG. 1 for OCT-enabled injection during vitreoretinal surgery, as disclosed herein. Also shown in surgical field 300 is a surgical tool 304 and surgical injector 116. The location at the retina that the user desires to inject a substance is given by a location 306, which the user may indicate to OCT scanning controller 150, as described above.

As described above, once the user specifies location 306, an OCT image (not shown) at location 306 may be generated and displayed to the user. For example, the OCT image may be displayed as a video overlay (not shown) in a portion of surgical field 300 that continuously updates at a given refresh rate. The OCT image may be a B-scan image or an en face image. Surgical injector 116 is typically formed as a metal syringe needle, and surgical injector 116 may appear in the OCT image with high contrast and may be detected in the OCT image, including a tip of surgical injector 116. Alternatively, surgical injector 116 may be formed of a polymer with one or more high-contrast features that may be detected in the OCT image.

Furthermore, an angle between sample beam 130 used for OCT and surgical injector 116 in the eye may be determined. For example, surgical injector 116 may be mounted to surgical microscope 120 in a fixed geometric relationship. A mounting attachment for fixing surgical injector 116 to surgical microscope 120 may then define the angular relationship between surgical injector 116 and sample beam 130/measurement beam 132, such as when surgical injector 116 is an automatic device capable of self-actuation of the injection. In another example, a calibration may be performed prior to the vitreoretinal surgery using a phantom surgical injector outside of eye 110 to calibrate the OCT image with a known reference angle. With knowledge of the angle, the precise location of the tip of surgical injector 116 may be determined using OCT.

Accordingly, even when surgical injector 116 is introduced at an oblique angle, the tip of surgical injector 116 may be identified relative to the tissue layers in depth at location 306 using image processing on the OCT image, as noted above. In this manner, a precise identification of the depth that surgical injector 116 penetrates a given tissue layer may be determined and used to trigger the injection of the substance by surgical injector 116, as disclosed herein.

Referring now to FIG. 4, a flow chart of selected elements of an implementation of a method 400 for OCT-enabled injection during vitreoretinal surgery, as described herein, is depicted in flowchart form. Method 400 describes steps and procedures that may be performed while surgical microscopy scanning instrument 100 is operated to view the fundus of an eye and perform surgical procedures based on the view of the fundus, including the use of surgical injector 116 to inject a given volume of a substance into the eye. Accordingly, at least certain portions of method 400 may be performed by injection control application 214. It is noted that certain operations described in method 400 may be optional or may be rearranged in different implementations. Method 400 may be performed by injection control application 214 to interact with a surgeon or other medical personnel, referred to herein as a "user".

Prior to method 400, it may be assumed that surgical microscopy scanning instrument 100 is being used to view an interior portion of an eye of a patient, such as described in FIG. 1. Then, method 400 may begin, at step 402, by receiving a first indication from a user of an ophthalmic visualization system of a location in the eye for receiving an injection of a substance. Based on the first indication, at step 404, OCT scanning of the location is initiated, the OCT scanning enabled to continuously generate an OCT image of tissue layers at the location. The OCT image may be a B-scan image or an en face image. At step 406, the OCT image is caused to be displayed to the user. At step 408, a second indication is received from the user to perform the injection at the location, where the second indication specifies a tissue layer from the OCT image for receiving the injection and a volume of the substance to be injected. The user may select the tissue layer for injection from the display of the OCT image. Based on the second indication, at step 410, a surgical injector is detected at the location from the OCT image, including detecting whether the surgical injector penetrates the tissue layer. For example, the tip of the surgical injector may be identified in the OCT image relative to the tissue layer. At step 412 a decision may be made whether the surgical injector penetrates the tissue layer. While step 412 is being performed, the user may insert the surgical injector into the eye and may begin to penetrate the tissue layer specified by the user in the second indication in step 408. When the result of step 412 is NO and the surgical injector does not penetrate the tissue layer, method 400 may return to step 412 for repetitive polling of step 412. When the result of step 412 is NO and the surgical injector does penetrate the tissue layer, at step 414, the injection is caused to be performed by the surgical injector, where the surgical injector injects the substance into the tissue layer. From the second indication, the surgical injector may be configured to inject the volume of the substance after step 408. At step 416, a feedback indication is caused to be output to the user, the feedback indication indicating confirmation of the injection of the volume.

As disclosed herein, OCT-enabled injection during vitreoretinal surgery may involve using an OCT image to detect when a surgical injector penetrates a desired tissue layer of the eye for receiving an injection. The injection may be triggered or automatically actuated based on the detection of the surgical injector from the OCT image.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for injecting substances during ophthalmic surgery, the method comprising:

during viewing of an interior portion of an eye of a patient using an ophthalmic visualization system, receiving a first indication from a user of the ophthalmic visualization system of a location in the eye for receiving an injection of a substance;

based on the first indication, initiating optical coherence tomography (OCT) scanning of the location, the OCT scanning enabled to continuously generate an OCT image of tissue layers at the location, wherein the OCT scanning is performed by an OCT scanner that is optically coupled to the ophthalmic visualization system;

causing the OCT image to be displayed to the user;

receiving a second indication from the user to perform the injection at the location, wherein the second indication specifies a tissue layer from the OCT image for receiving the injection and a volume of the substance to be injected;

based on the second indication, detecting a surgical injector at the location from the OCT image, including detecting whether the surgical injector penetrates the tissue layer; and when the surgical injector penetrates the tissue layer, causing the injection to be performed by the surgical injector, wherein the surgical injector injects the volume of the substance into the tissue layer.

2. The method of claim 1, wherein receiving the second indication further comprises:

receiving final approval for automatically causing the injection to be performed based only on detecting that the surgical injector has penetrated the tissue layer.

3. The method of claim 1, wherein receiving the second indication further comprises:

receiving a confirmation from the user that the surgical injector is being armed to automatically perform the injection.

4. The method of claim 1, wherein the location is in a posterior portion of the interior portion of the eye.

5. The method of claim 1, wherein the tissue layer is one of: an intraretinal layer; and a subretinal layer.

6. The method of claim 1, wherein the surgical injector is one of: a metal syringe needle, a polymer needle, a metal cannula, and a polymer cannula, and wherein the OCT image is one of: a B-scan image and an en face image.

7. The method of claim 1, wherein causing the OCT image to be displayed to the user further comprises:

causing the OCT image to be displayed to the user in a surgical field of the ophthalmic visualization system.

8. The method of claim 1, wherein the substance comprises at least one of: cells, photoreceptor aggregates, viral vectors, nucleic acids, proteins, peptides, peptidomimetics, small molecules, large molecules, nanostructures and nanoparticles.

9. The method of claim 1, further comprising:

after causing the OCT image to be displayed to the user, enabling the user to specify the tissue layer using the OCT image.

10. The method of claim 1 further comprising:

after the surgical injector injects the volume of the substance into the tissue layer, causing a feedback indication to be output to the user, the feedback indication indicating confirmation of the injection of the volume and comprising at least one of: an audio alert; and a visual alert in a surgical field of the ophthalmic visualization system.

* * * * *